United States Patent
Sale et al.

(10) Patent No.: US 11,565,991 B2
(45) Date of Patent: Jan. 31, 2023

(54) MIXTURE OF BISPHOSPHITES HAVING AN OPEN AND A CLOSED OUTER UNIT AND THE USE THEREOF AS A CATALYST MIXTURE IN HYDROFORMYLATION

(71) Applicant: EVONIK OPERATIONS GMBH, Essen (DE)

(72) Inventors: Anna Chiara Sale, Recklinghausen (DE); Robert Franke, Marl (DE); Alexander Brächer, Haltern am See (DE); Dirk Fridag, Haltern am See (DE); Johannes Knossalla, Gahlen (DE); Peter Kucmierczyk, Herne (DE); Ana Markovic, Haltern am See (DE)

(73) Assignee: EVONIK OPERATIONS GMBH, Essen (DE)

( * ) Notice: Subject to any disclaimer, the term of this patent is extended or adjusted under 35 U.S.C. 154(b) by 0 days.

(21) Appl. No.: 17/718,542

(22) Filed: Apr. 12, 2022

(65) Prior Publication Data

US 2022/0340511 A1 Oct. 27, 2022

(30) Foreign Application Priority Data

Apr. 16, 2021 (EP) .................................. 21168814.8

(51) Int. Cl.
*B01J 31/02* (2006.01)
*C07C 45/50* (2006.01)
*B01J 31/22* (2006.01)

(52) U.S. Cl.
CPC ........... *C07C 45/50* (2013.01); *B01J 31/0257* (2013.01); *B01J 31/2213* (2013.01); *B01J 2231/321* (2013.01); *B01J 2531/822* (2013.01)

(58) Field of Classification Search
CPC ................ C07C 45/505; B01J 31/0257; B01J 2231/321
See application file for complete search history.

(56) References Cited

U.S. PATENT DOCUMENTS 9,670,108 B2 * 6/2017 Dyballa ................ C07F 15/008
2022/0089623 A1 3/2022 Sale et al.

FOREIGN PATENT DOCUMENTS

| EP | 0 213 639 A2 | 3/1987 |
| JP | H08-165266 A | 6/1996 |
| WO | 2008/115740 A1 | 9/2008 |

OTHER PUBLICATIONS

R. Franke, et al. "Applied Hydroformylation" Chemical Reviews, 2012, pp. 5675-5732.
U.S. Appl. No. 17/718,525, filed Apr. 12, 2022.
U.S. Appl. No. 17/718,503, filed Apr. 12, 2022.
U.S. Appl. No. 17/696,038, filed Mar. 16, 2022.
European Search Report dated Sep. 3, 2021 for European Patent Application No. 21168814.8 (8 pages in German with machine translation).
Van Rooy, A., et al. Bulky Diphosphite-Modified Rhodium Catalysts: Hydroformylation and Characterization. Organometallics. 1996. vol. 15, pp. 835-847.

* cited by examiner

*Primary Examiner* — Sikarl A Witherspoon
(74) *Attorney, Agent, or Firm* — Smith, Gambrell & Russell, LLP

(57) ABSTRACT

Mixture of bisphosphites having an open and a closed outer unit and the use thereof as a catalyst mixture in hydroformylation.

6 Claims, No Drawings

MIXTURE OF BISPHOSPHITES HAVING AN OPEN AND A CLOSED OUTER UNIT AND THE USE THEREOF AS A CATALYST MIXTURE IN HYDROFORMYLATION

The invention relates to a mixture of bisphosphites having an open and a closed outer unit and the use thereof as a catalyst mixture in hydroformylation.

The reactions between olefin compounds, carbon monoxide and hydrogen in the presence of a catalyst to afford the aldehydes comprising one more carbon atom are known as hydroformylation or the oxo process. In these reactions, compounds of the transition metals of group VIII of the Periodic Table of the Elements are frequently employed as catalysts. Known ligands are, for example, compounds from the phosphine, phosphite and phosphonite classes, each containing trivalent phosphorus $P^{III}$. A good overview of the state of the art of hydroformylation of olefins may be found in R. Franke, D. Selent, A. Börner, "Applied Hydroformylation", Chem. Rev., 2012, DOI:10.1021/cr3001803.

The technical problem addressed by the present invention is that of providing a ligand mixture which exhibits a good n/iso selectivity and also provides a good yield in the hydroformylation of olefins.

The problem is solved by a mixture according to Claim 1.
Mixture comprising the compounds (1A) and (1B):

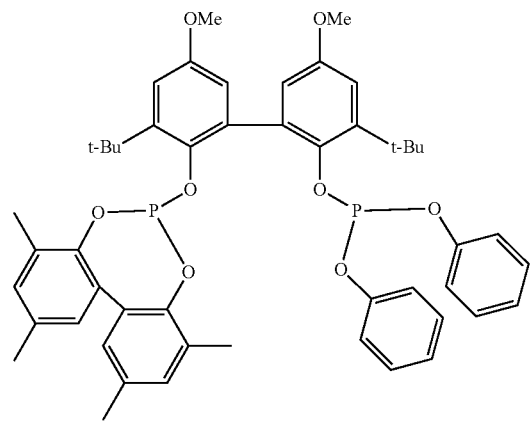

(1A)

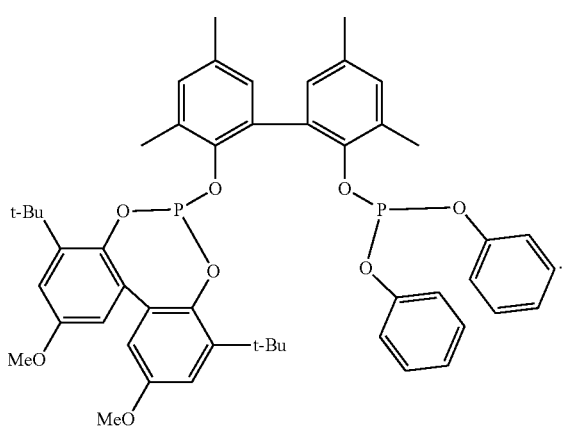

(1B)

In one embodiment, the content of compound (1A) is in a range from 99.5% to 0.5% by mass and the content of compound (1B) is in a range from 0.5% to 99.5% by mass.

In one embodiment, the content of compound (1A) is in a range from 75% to 25% by mass and the content of compound (1B) is in a range from 25% to 75% by mass.

In one embodiment, the content of compound (1A) in terms of % by mass is greater than the content of compound (1B).

As well as the mixture per se, the use thereof for catalysis of a hydroformylation reaction is also claimed.

Use of a mixture as described above for catalysis of a hydroformylation reaction.

Also claimed is a process in which a mixture as described above is used as a ligand mixture.

Process comprising the process steps of:
a) initially charging an olefin,
b) adding a mixture as described above and a substance comprising a metal selected from: Rh, Ru, Co, Ir,
c) supplying $H_2$ and CO,
d) heating the reaction mixture from steps a) to c), to convert the olefin into an aldehyde.

In a preferred embodiment, the metal is Rh.

In a variant of the process, the substance in process step b) is selected from: $Rh(acac)(CO)_2$, [(acac)Rh(COD)] (Umicore, acac=acetylacetonate anion; COD=1,5-cyclooctadiene), $Rh_4CO_{12}$.

The ligands can also be used in excess here and it is not automatically the case that each ligand is present in bound form as a ligand-metal complex; it may instead be present in the reaction mixture as the free ligand.

The reaction is carried out under customary conditions.

Preference is given to a temperature of 80° C. to 160° C. and a pressure of 10 to 60 bar.

Particular preference is given to a temperature of 100° C. to 140° C. and a pressure of 20 to 50 bar.

The reactants for the hydroformylation in the process of the invention are olefins or mixtures of olefins, especially monoolefins having 2 to 24, preferably 3 to 16 and more preferably 3 to 12 carbon atoms, and having terminal or internal C—C double bonds, for example 1-propene, 1-butene, 2-butene, 1- or 2-pentene, 2-methyl-1-butene, 2-methyl-2-butene, 3-methyl-1-butene, 1-, 2- or 3-hexene, the $C_6$ olefin mixture obtained in the dimerization of propene (dipropene), heptenes, 2- or 3-methyl-1-hexenes, octenes, 2-methylheptenes, 3-methylheptenes, 5-methyl-2-heptene, 6-methyl-2-heptene, 2-ethyl-1-hexene, the Ca olefin mixture obtained in the dimerization of butenes (di-n-butene, diisobutene), nonenes, 2- or 3-methyloctenes, the $C_9$ olefin mixture obtained in the trimerization of propene (tripropene), decenes, 2-ethyl-1-octene, dodecenes, the $C_{12}$ olefin mixture obtained in the tetramerization of propene or the trimerization of butenes (tetrapropene or tributene), tetradecenes, hexadecenes, the $C_{16}$ olefin mixture obtained in the tetramerization of butenes (tetrabutene), and olefin mixtures having different numbers of carbon atoms (preferably 2 to 4) produced by cooligomerization of olefins.

The process of the invention using the ligands of the invention can be used for the hydroformylation of α-olefins, terminally branched, internal and internally branched olefins.

The invention is to be illustrated in detail hereinafter by a working example.

Operating Procedures
General Analysis

All the preparations that follow were carried out under inert gas using standard Schlenk techniques. The solvents were dried before use over suitable drying agents.

The products were characterized by NMR spectroscopy. Chemical shifts (δ) are reported in ppm. The $^{31}$P NMR signals were referenced as follows: $SR^{31}P = SR^1H*(BF^{31}P/BF^1H) = SR^1H*0.4048$.

Synthesis Procedures

Precursors (3A) and (3B):

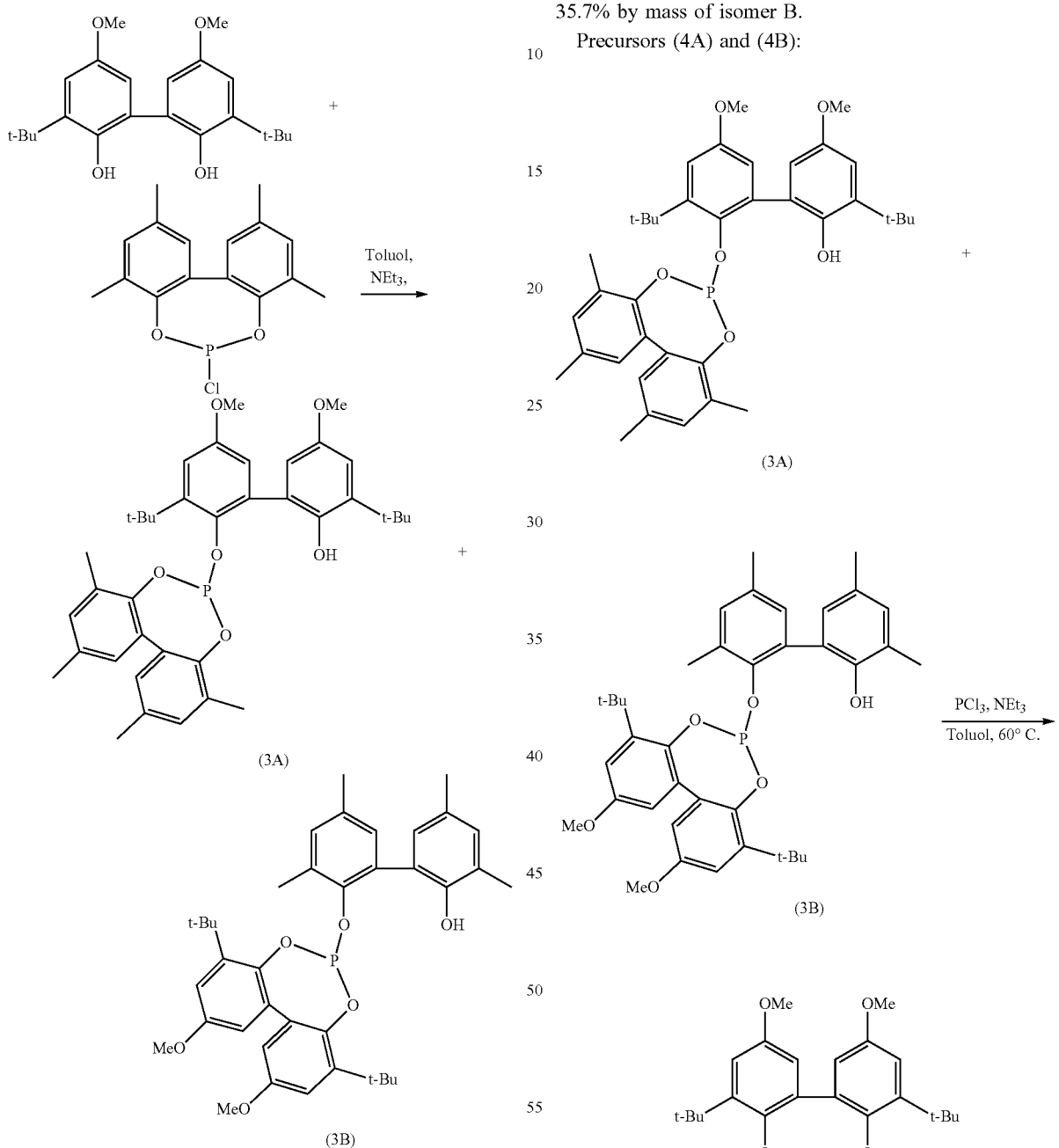

In a 500 ml Schienk flask 10.7 g (0.03 mol) of 3,3'-di-tert-butyl-2,2'-dihydroxy-5,5'-dimethoxybiphenyl were initially charged and admixed with 125 mL of toluene with stirring. A suspension was formed. In a glovebox 10 g of the chlorophosphite were weighed into a 250 mL Schienk flask and evacuated. The chlorophosphite was likewise dissolved in 125 mL of toluene with stirring and admixed with (0.035 mol) of Et$_3$N. The chlorophosphite-base-toluene solution prepared was subsequently added dropwise to the 3,3'-di-tert-butyl-2,2'-dihydroxy-5,5'-dimethoxybiphenyl suspension over 1 h with vigorous stirring at room temperature. The reaction mixture was subsequently stirred for 24 h. The hydrochloride was then filtered off via a frit and the filtrate concentrated to dryness using an oil pump vacuum. The solid was then introduced into the glovebox.

Total yield 92%. Thereof: 64.3% by mass of isomer A and 35.7% by mass of isomer B.

Precursors (4A) and (4B):

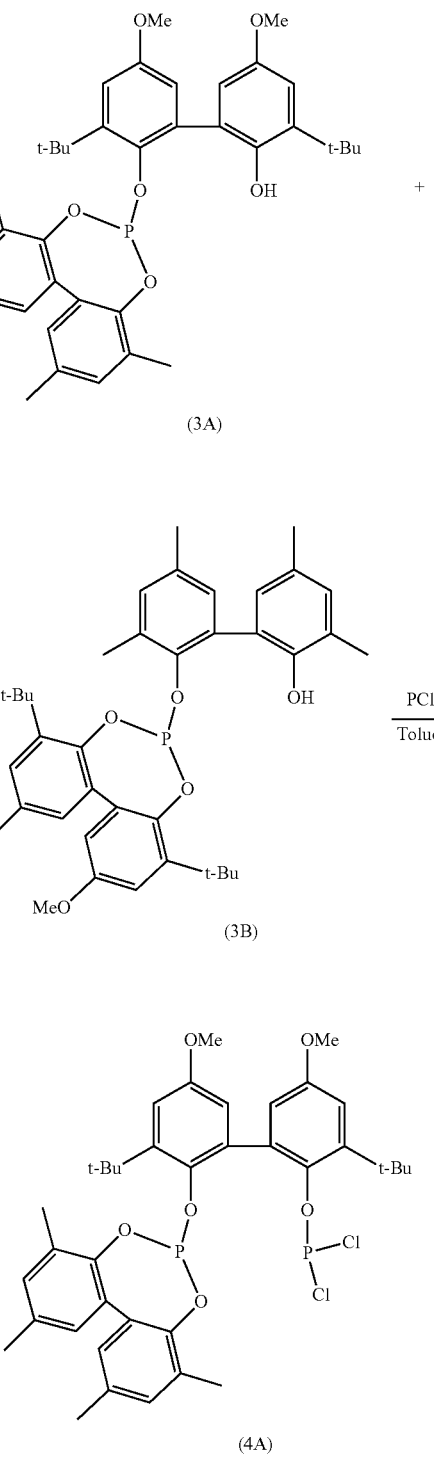

-continued

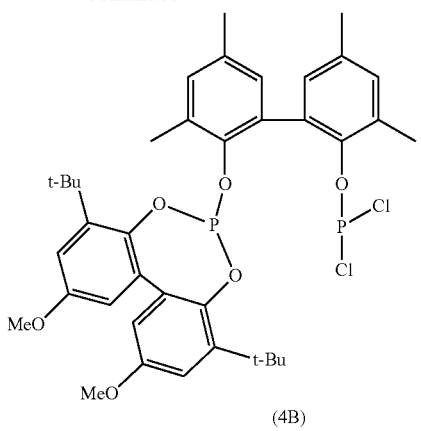

(4B)

19 g (0.027 mol) of the isomer mixture of (3A) and (3B) obtained previously were weighed into a purged 250 mL Schlenk flask in the glovebox. After removal from the glovebox, 160 mL of dried toluene and, by means of an argon-purged syringe, 12 mL=8.8 g (0.086 mol) of degassed triethylamine were added to the solid with stirring.

In a second 500 ml Schienk flask initially 100 mL of dried toluene were initially charged before 7.7 mL=12 g (0.086 mol) of phosphorus trichloride were added by means of an argon-purged syringe with stirring. Subsequently, with vigorous stirring, the phosphite/amine/toluene solution prepared previously was added dropwise to the phosphorus trichloride/toluene solution over 25 minutes at room temperature. Once addition was complete the reaction mixture was heated to 60° C. and stirred at this temperature overnight. After cooling to room temperature the resulting amine hydrochloride was filtered off via a frit. The filtrate was concentrated to dryness at 55° C. using an oil pump vacuum and the obtained solid dried further overnight.

Total yield 90%. Thereof: 64.7% by mass of isomer A and 35.3% by mass of isomer B.

Mixture of (1A) and (1B):

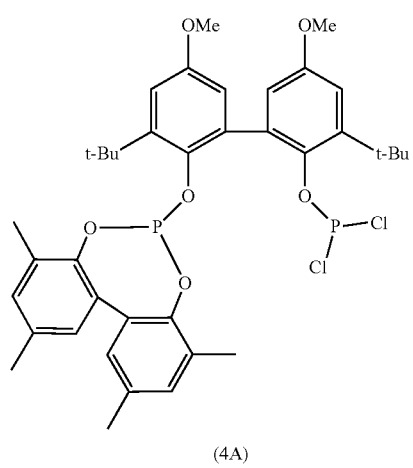

(4A)

-continued

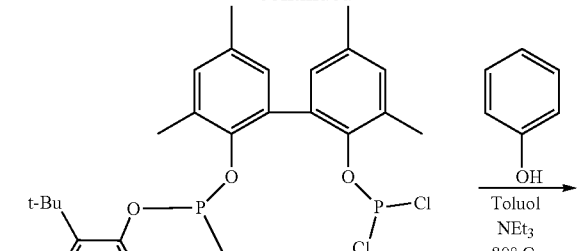

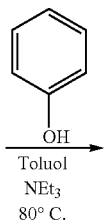

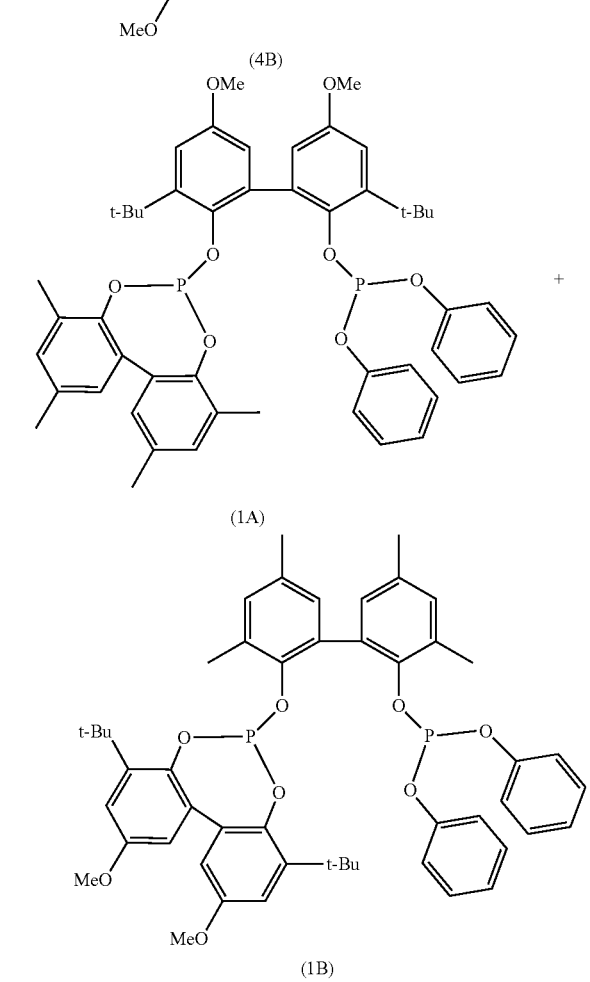

(1A)

(1B)

In the glovebox 8 g (0.01 mol) of diorganophosphite dichlorophosphite mixture of (4A) and (4B3) as obtained previously were weighed into a purged 250 ml Schlenk flask, then evacuated and dissolved in 75 mL of dried toluene. In a second purged 250 ml Schlenk flask 1.9 g (0.02 mol) of phenol were weighed out and dried further at room temperature overnight using an oil pump vacuum. The following morning 50 ml of dried toluene and 6 mL=4.4 g (0.044 mol) of degassed triethylamine were added with stirring and the solids dissolved with stirring. The chlorophosphite solution prepared previously was then added to the phenol-triethylamine solution in one go. The reaction mixture was then immediately heated to 80° C. and stirred at this reaction temperature overnight. After cooling to room temperature the resulting amine hydrochloride was filtered off via a frit at room temperature. For better filterability of the amine hydrochloride the stirrer was first switched off and the reaction mixture allowed to stand for 1.5 h. The obtained filtrate was concentrated to dryness and subjected to further drying at room temperature over the weekend using an oil pump vacuum. The obtained solid was admixed with 100 ml of degassed heptane with stirring and heated to 70° C. The mixture was stirred for 1.5 h at 70° C. and brought to room temperature with stirring. The cloudy solution was filtered via a frit. The clear filtrate was concentrated to dryness.

Purification:

To achieve chlorine reduction the product was dissolved in about 20 ml of dried toluene. The substance was subsequently filtered via a frit filled with silica gel under an argon atmosphere. The silica gel was first slurried into a 600 ml beaker using dried toluene and transferred into the frit. Dried toluene was used as the mobile phase. About 500 ml of dried toluene were used as the mobile phase for this operation. The obtained filtrate was then concentrated to dryness.

Chlorine determination: <20 ppm

Total yield 35%. Thereof: 54.3% by mass of isomer A and 45.7% by mass of isomer B.

Mixture of (2A) and (2B) (comparative mixture):

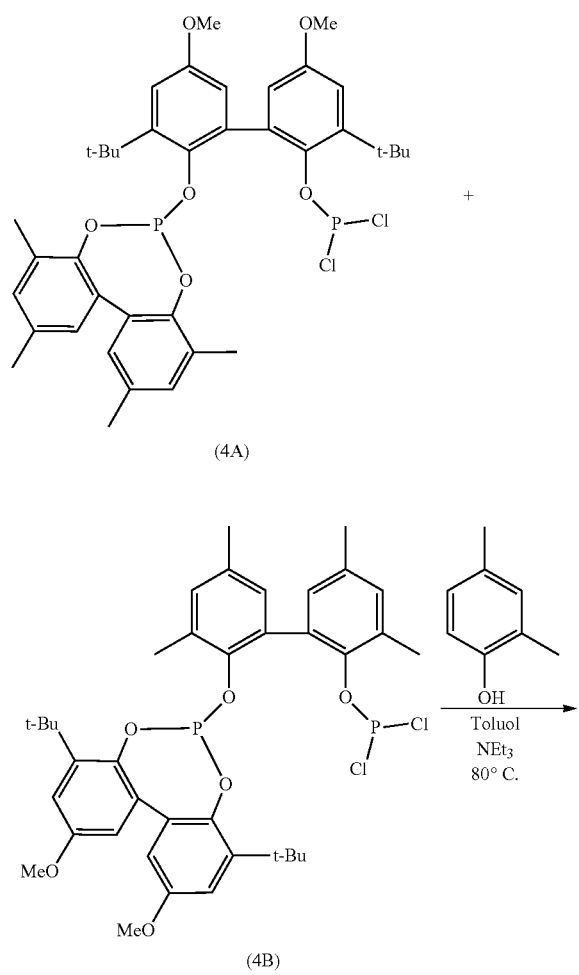

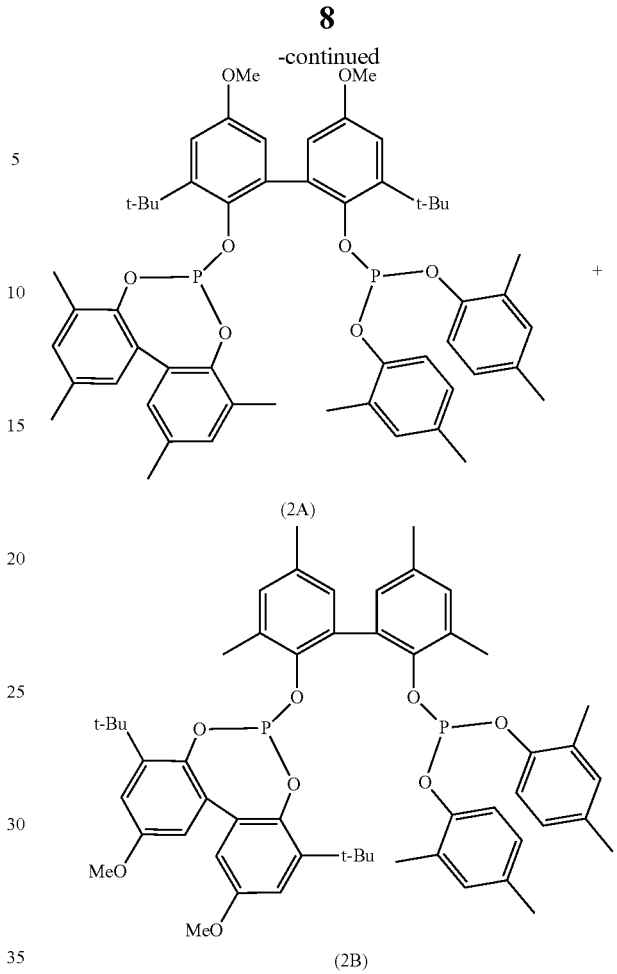

Synthesis and purification were carried out analogously to (1A) and (1B) but with the exception that accordingly 2.45 g (0.02 mol) of 2.4-dimethylphenol were weighed out.

Total yield 26%. Thereof: 59.3% by mass of isomer A and 40.7% by mass of isomer B.

Catalysis Experiments

The hydroformylation was carried out in a 16 ml autoclave from HEL Group, Hertfordshire, Great Britain, equipped with a constant-pressure apparatus, gas flowmeter and sparging stirrer. The n-octene used as substrate (Oxeno GmbH, mixture of octene isomers of 1-octene: 3%; cis+trans-2-octene: 49%; cis+trans-3-octene: 29%; cis+trans-4-octene: 16%; structurally isomeric octenes: 3%) was heated under reflux for several hours over sodium and distilled under argon.

The reaction solutions for the experiments were prepared beforehand under an argon atmosphere. To this end, 0.0021 g of Rh(acac)(CO)$_2$ and the corresponding amount of phosphite compound were weighed in and made up with 8.0 ml of toluene. The mass of toluene introduced in each case was determined for the GC analysis. 1.80 g of n-octene (16 mmol) were then added. The prepared solutions were then introduced into the autoclave and said autoclave was purged three times with argon and three times with synthesis gas (Linde; H$_2$ (99.999%):CO (99.997%)=1:1). The autoclave was then heated to the desired temperature at an overall pressure of 10 bar with stirring (900 rpm). Upon achieving the reaction temperature, the synthesis gas pressure was increased to 20 bar and the reaction was carried out for 4 h at constant pressure. Once the reaction time had elapsed the autoclave was cooled to room temperature, decompressed with stirring and purged with argon. 0.5 ml of each reaction mixture was withdrawn after termination of the reaction, diluted with 4 ml of pentane and analysed by gas chromatography: HP 5890 Series II plus, PONA, 50 m×0.2 mm×0.5 µm. Residual olefin and aldehyde were quantitatively determined against the solvent toluene as internal standard.

Result of the Catalysis Experiments

[Rh]: 120 ppm, L:Rh=1:2, p: 20 bar, T: 120° C.; t: 4 h

TABLE

Hydroformylation of n-octenes

| Ligand mixtures | n/iso selectivity in % | Yield |
|---|---|---|
| 1A + 1B* | 78 | 21% |
| 2A + 2B | 75 | 17% |

*inventive mixture

Definition of Selectivity:

In hydroformylation n/iso selectivity is the ratio of linear aldehyde (=n) to branched aldehyde (=iso). The selectivity for n-aldehyde indicates that this amount of linear product was formed. The remaining percentages then correspond to the branched isomer. Thus, at a regioselectivity of 50% n-aldehyde and iso-aldehyde are formed in equal proportions.

The inventive mixture (1A) and (1B) achieved an increased selectivity and yield relative to the comparative mixture of (2A) and (25).

The tests performed demonstrate that the problem addressed is solved by a mixture according to the invention.

The invention claimed is:

1. A mixture comprising the compounds (1A) and (1B):

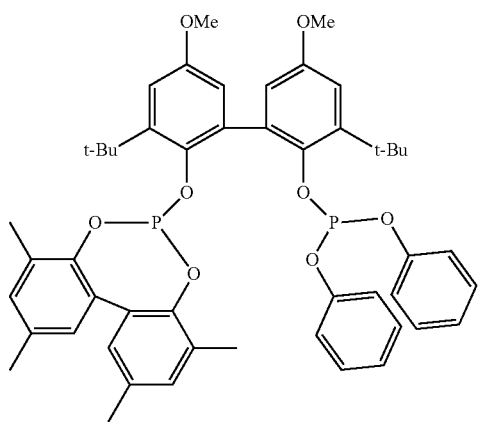

(1A)

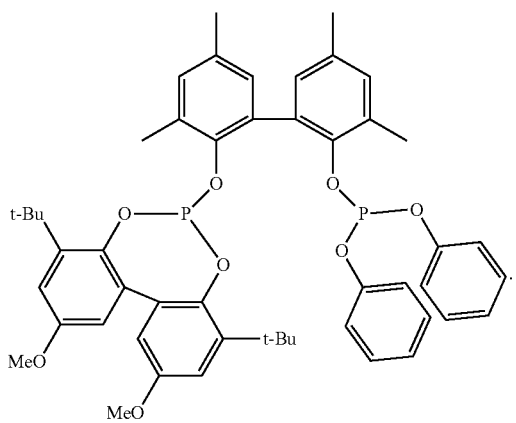

(1B)

2. The mixture according to claim 1, wherein the content of compound (1A) is in a range from 99.5% to 0.5% by mass and the content of compound (1B) is in a range from 0.5% to 99.5% by mass.

3. The mixture according to claim 1, wherein the content of compound (1A) is in a range from 75% to 25% by mass and the content of compound (1B) is in a range from 25% to 75% by mass.

4. The mixture according to claim 1, wherein the content of compound (1A) in terms of % by mass is greater than the content of compound (1B).

5. A composition comprising a mixture according to claim 1 and a substance comprising a metal selected from: Rh, Ru, Co or Ir.

6. A process comprising the process steps of:

a) initially charging an olefin, b) adding a mixture according to claim 1 and a substance comprising a metal selected from: Rh, Ru, Co or Ir, c) supplying $H_2$ and CO, and d) heating the reaction mixture from steps a) to c), to convert the olefin into an aldehyde.

* * * * *